United States Patent [19]

Ellis

[11] 4,088,445

[45] May 9, 1978

[54] COMBINATION NIGHT LIGHT AND STERILIZING HOLDER FOR TOILET ARTICLES

[76] Inventor: Douglas G. Ellis, 10708 SE. Home, Milwaukie, Oreg. 97222

[21] Appl. No.: 758,942

[22] Filed: Jan. 13, 1977

[51] Int. Cl.² ............................................... A61L 3/00
[52] U.S. Cl. ...................................... 21/83; 21/102 R; 250/455
[58] Field of Search ............... 312/206; 21/83, 102 R; 250/455

[56] References Cited

U.S. PATENT DOCUMENTS

| | | | |
|---|---|---|---|
| 2,180,213 | 11/1939 | Peake | 21/83 |
| 2,592,131 | 4/1952 | Farrar | 21/102 R X |
| 3,114,038 | 12/1963 | Meader | 21/83 |
| 3,309,159 | 3/1967 | Le Sueur et al. | 21/102 R |
| 3,342,544 | 9/1967 | Curiel | 21/83 |
| 3,353,905 | 11/1967 | Ellis | 21/83 X |
| 3,954,407 | 5/1976 | Andary et al. | 21/83 |

Primary Examiner—Morris O. Wolk
Assistant Examiner—Roger F. Phillips
Attorney, Agent, or Firm—Eugene M. Eckelman

[57] ABSTRACT

A hollow body member has a plurality of side opening pockets at the upper portion thereof to receive toilet articles such as toothbrushes. The inner ends of the pockets have openings into the interior of the body member providing exposure to sterilizing radiation from an uncoated portion of a light bulb supported within the housing. The light emitted from the coated portion serves as a night light. At the top of the holder is a shelf for supporting containers thereon in inverted relation whereby the containers are also sterilized by the bulb.

3 Claims, 3 Drawing Figures

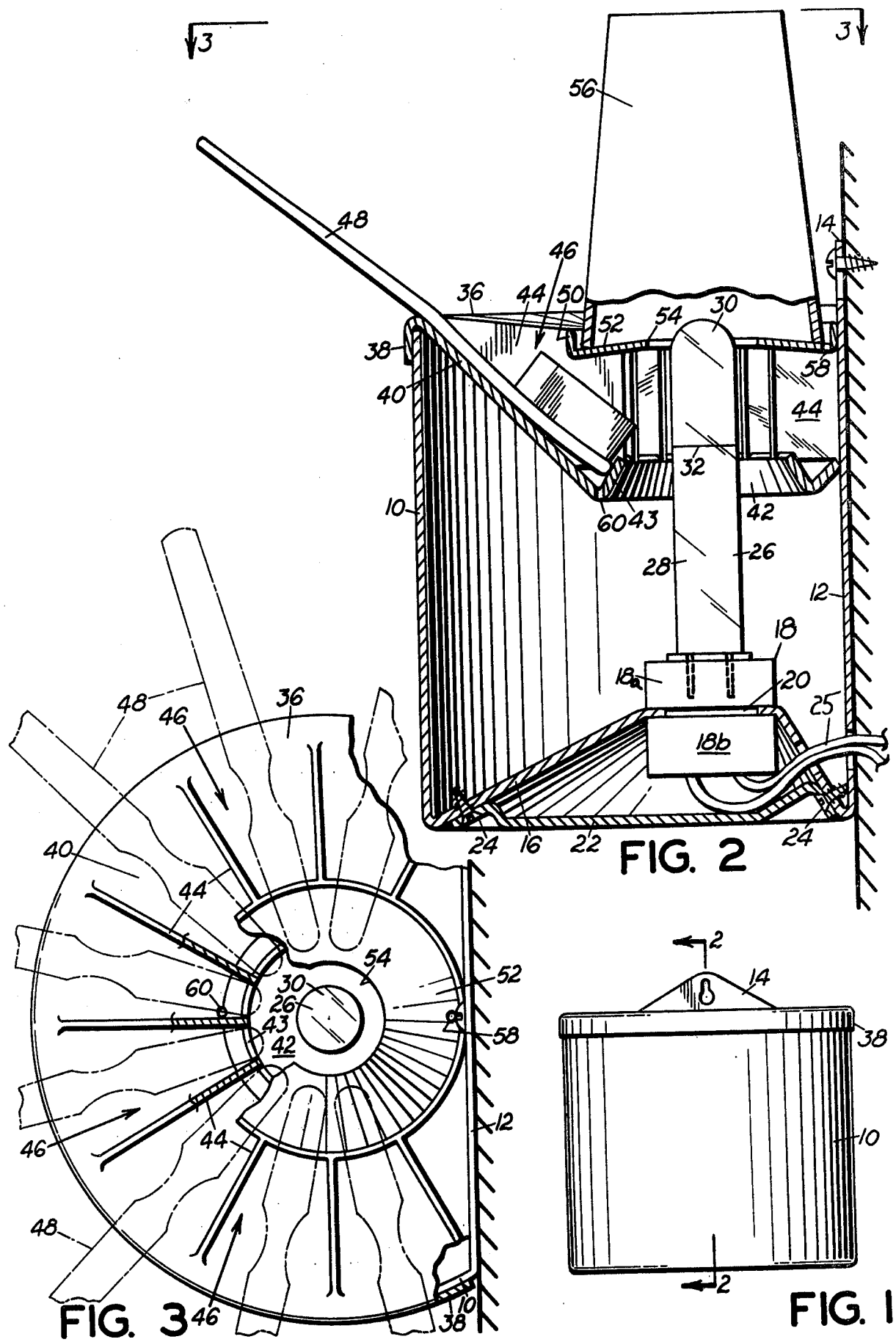

COMBINATION NIGHT LIGHT AND STERILIZING HOLDER FOR TOILET ARTICLES

BACKGROUND OF THE INVENTION

This invention relates to new and useful improvements in a combination night light and sterilizing holder for toilet articles.

Holders have heretofore been provided for toilet articles which not only provide storage therefor when not in use but also provide means in the holder for sterilizing the toilet articles. Such previous holders have disadvantages one of which is that the toilet articles are not held in a convenient position for insertion and removal. Another disadvantage is that the holders cannot be readily cleaned on the inside and otherwise readily maintained for efficient usage. Still another disadvantage is that the electric circuitry in the sterilizing means is not substantially concealed to prevent tampering therewith by children.

SUMMARY OF THE INVENTION

According to the present invention and forming a primary objective thereof, a combination night light and sterilizing holder for toilet articles is provided that overcomes the above enumerated disadvantages.

More particularly, the holder of the instant invention utilizes a hollow body member which supports and substantially conseals a sterilizing bulb therein as well as its wiring. The body member has a top wall provided with downwardly inclined radial pockets which hold toilet articles for convenient insertion and removal. The inner ends of the pockets open into the interior of the body member, and an upper sterilizing portion of the bulb extends vertically in the plane of such openings for sterilizing the toilet articles. An upper shelf on the top wall is provided for supporting a container in inverted relation, and such shelf has an opening therein through which rays from the bulb can sterilize the container. The top wall is removable for access to the interior of the holder.

BRIEF DESCRIPTION OF THE DRAWINGS

FIG. 1 is a front elevational view of a combination night light and sterilizing holder for toilet articles embodying features of the present invention;

FIG. 2 is an enlarged vertical sectional view of the holder taken on the line 2—2 of FIG. 1; and FIG. 3 is an enlarged top plan view, partly broken away, taken on the line 3—3 of FIG. 2.

DETAILED DESCRIPTION OF A PREFERRED EMBODIMENT

With particular reference to the drawings, the present holder comprises a hollow body member 10 which may be of any suitable shape but which for purposes of illustration is shown substantially circular but having a flat rear wall portion 12 which can abut against a wall if it is desired that the holder be hung on a wall. Support on a wall may be provided by any suitable means such as by adhesive attachment to the wall or by screw attachment through an upwardly projecting tab 14 on the back wall.

The body member 10 has a raised bottom wall 16 arranged to detachably receive a socket 18 which preferably comprises two parts 18a and 18a having threaded detachable connection in an aperture 20 in the bottom wall. The bottom wall 16 is raised sufficiently to enclose the socket portion 18b thereunder, and the bottom of the holder is closed by a plate 22 removably attached as by screws 24. Wires 25 preferably lead in through the rear wall 12 and are mostly enclosed in the area between the wall 16 and plate 22 so as to be substantially non-accessible to children.

A fluorescent and sterilizing bulb 26 is removably mounted in the socket 18 and projects vertically in the holder. When referring to a fluorescent and sterilizing bulb, it is meant it is a mercury vapor type bulb which is interiorly partially coated with chemicals which when fired is capable of transmitting visible light through the coated portion and ultraviolet rays through the uncoated portion. Such ultraviolet rays are trapped within the lighting tube by the coatings in the tube, and for the purposes of the present invention a lower portion 28 of the tube is coated and an upper portion 30 of the tube is uncoated, the demarcation between the coated and uncoated portions being designated by the numeral 32. Thus, ultra-violet rays can be transmitted through the tube at the uncoated portion 30 but are trapped within the tube at the coated portion 28.

A top wall 36 seats on the body member 10 and has a depending flange 38 around the side and front thereof which fits partly down over the body member 10. Flange 38 preferably has a friction fit on the body member whereby the top wall can be removed to provide access to the interior of the body member.

The top wall 36 has a downwardly inclined or frusto-conical wall portion 40 which terminates short of the center of the body member to form an opening 42 through which the bulb 28 projects. The inner end of wall portion 40 is upturned at 43. A plurality or radially extending vertical walls or partitions 44 are integral with the bottom wall 40 and form pockets 46 in such bottom wall for receiving toilet articles 48 such as toothbrushes therein. Since the bottom wall 40 of the pocket is angled downwardly, the toothbrushes will remain in the pockets by gravity engaged against upturned wall 43. The handles of the toothbrushes project upwardly for easy grasping.

The top edge portions of the radial walls 44 are notched at 50 adjacent their inner end, and a flanged shelf 52 is integral with such notched edges. This shelf has a central aperture 54 and inclines downwardly toward the outside of the holder whereby drippings from a container 56 supported in inverted relation on the shelf flow outwardly. One or more drain openings 58 are provided at the outer end of the shelf to discharge drippings down into the holder, and furthermore one or more drain openings 60 are provided in bottom wall 40 at the base of upturned end 43 for discharging drippings from above, or from the toilet articles in the pockets, into the bottom of the holder.

As apparent in FIG. 1, the bulb 26 projects up through the opening 42 and the uncoated portion 30 thereof is in the area of the pockets 46 whereby outwardly directed ultra-violet rays are adapted to sterilize toilet articles placed in the pockets 46. Such toilet articles are thus sterilized during their periods of non-use. Furthermore, the uncoated portion of the bulb projects upwardly at least as high as or even above the opening 54 of the shelf 52 so that a container such as a drinking glass will also be sterilized during its period of non-use. The bulb also will emit sufficient light to serve as a night light. With the particular construction of the top wall 36 and with toilet articles placed in the pockets, as well as a glass or cup placed on the shelf 52, there will be no glare exteriorly of the holder.

It is to be understood that the form of my invention herein shown and described is to be taken as a preferred example of the same and that various changes in the shape, size and arrangement of parts may be resorted to without departing from the spirit of my invention, or the scope of the subjoined claims.

Having thus described my invention, I claim:

1. A combination night light and sterilizing holder for toilet articles comprising
   (a) a hollow body portion having surrounding side walls and a bottom wall,
   (b) a top wall on said body member having a vertical opening therein,
   (c) radially extending vertical partition means on said top wall around a portion of said opening and forming pockets which are open at their outward ends for receiving toilet articles and which are also open at their inward ends,
   (d) means on said cover arranged to limit inward positioning of toilet articles in said pockets,
   (e) shelf means on said cover disposed above said vertical opening for supporting a container in inverted relation,
   (f) a vertical opening in said shelf means aligned vertically with the opening in said top wall,
   (g) a light bulb socket on said bottom wall,
   (h) and a sterilizing light bulb in said socket projecting through said opening in the top wall and extending at its upper end to a height adjacent said opening in the shelf means,
   (i) said bulb having a lower coated portion serving as a night light,
   (j) said bulb having an upper uncoated portion extending from its upper end down to an area adjacent the inward open ends of said pockets to direct sterilizing rays through the open inner ends of said pockets to sterilize toilet articles therein and also to direct sterilizing rays upward through the opening in said shelf means to sterilize a container on the shelf means.

2. The combination night light and sterilizing holder for toilet articles of claim 1 wherein said top wall and said shelf means are inclined downwardly toward the interior of said body member, and drain means in said top wall and shelf means at a lower portion thereof to drain off liquids from a container on the shelf means or toilet articles in the pockets.

3. The combination night light and sterilizing holder for toilet articles of claim 1 wherein said top wall is removable to provide access to the interior of said body member.

* * * * *